US 6,748,793 B2

(12) United States Patent
Rabinovich et al.

(10) Patent No.: US 6,748,793 B2
(45) Date of Patent: Jun. 15, 2004

(54) ULTRASOUND SENSING OF CONCENTRATION OF METHANOL'S AQUEOUS SOLUTION

(75) Inventors: Arnold Rabinovich, Cary, NC (US); Daryl Tulimieri, Raleigh, NC (US)

(73) Assignees: E. I. du Pont de Nemours and Company, Wilmington, DE (US); ABB Research Ltd., Zurich (CH)

( * ) Notice: Subject to any disclaimer, the term of this patent is extended or adjusted under 35 U.S.C. 154(b) by 0 days.

(21) Appl. No.: 10/033,416

(22) Filed: Dec. 28, 2001

(65) Prior Publication Data

US 2003/0121315 A1 Jul. 3, 2003

(51) Int. Cl.[7] .......................... G01N 33/20; G01N 37/00
(52) U.S. Cl. .................... 73/61.45; 73/61.45; 73/61.49; 73/597; 340/632
(58) Field of Search ................. 73/61.45, 597, 73/61.49; 340/632

(56) References Cited

U.S. PATENT DOCUMENTS

| 5,060,507 A | * | 10/1991 | Urmson et al. ............ 73/24.01 |
|---|---|---|---|
| 5,176,320 A | | 1/1993 | Kraus et al. |
| 5,537,854 A | | 7/1996 | Phillips et al. ............. 73/24.01 |
| 5,581,014 A | | 12/1996 | Douglas ................... 73/24.01 |
| 5,868,859 A | | 2/1999 | Hei et al. |
| 5,936,160 A | * | 8/1999 | Salo ........................... 73/597 |
| 6,067,840 A | | 5/2000 | Chelvayohan et al. |
| 6,306,285 B1 | | 10/2001 | Narayanan et al. |
| 6,308,572 B1 | | 10/2001 | Ishikawa et al. |

OTHER PUBLICATIONS

Perkin–Elmer Ltd, "Horizontal ATR Accessory," *Perkin–Elmer Spectrum 2000 FT–IR Manual*, 1995, 1–11, Jun. 1994.

* cited by examiner

*Primary Examiner*—Helen Kwok
*Assistant Examiner*—André K. Jackson

(57) ABSTRACT

Systems and methods for ultrasound sensing a compound's concentration in aqueous solution are provided. As a result of the ultrasound sensing, an accurate real time measurement of the concentration of the compound of interest in aqueous solution is obtained. In various non-limiting embodiments, the invention provides ultrasound sensing of methanol's concentration in aqueous solution in connection with a fuel circulation process for a direct methanol fuel cell. Since the speed of sound in a water-methanol system increases significantly with methanol content, techniques for measuring characteristic sound velocities are used to give sufficient resolution for a fuel circulation process.

26 Claims, 5 Drawing Sheets

ULTRASOUND SENSING OF CONCENTRATION OF METHANOL'S AQUEOUS SOLUTION

FIELD OF THE INVENTION

The present invention relates generally to the field of sensing the concentration of an aqueous solution. More particularly, the present invention relates to ultrasound sensing of the concentration of methanol's aqueous solution in connection with a fuel circulation loop of a direct methanol fuel cell.

BACKGROUND OF THE INVENTION

A direct methanol fuel cell (DMFC) is a type of polymer electrolyte membrane fuel cell (PEMFC). A DMFC operates at low internal temperature (~80 C.) and fuel is a non-flammable dilute methanol/water mixture, closely approximating auto windshield wiper fluid. There are no Environmental Protection Agency (EPA) regulated emissions in connection with using a DMFC, allowing for continuous operation. By some estimates, projected engineering power density for DMFCs is 10–20 Watts per liter.

PEMFCs, such as DMFCs, provide low temperature operation, cleanliness, safety, quiet performance, ease of operation, low maintenance, portability, modularity, scalability, responsiveness and versatility. The 'direct' aspect of DMFCs implies the elimination of a fuel reformer component, which simplifies the overall fuel system, lowering cost, making for a smaller assembly and further increasing efficiency. Due to the versatility of DMFCs, they may be used, e.g., to power transceiver stations for remote mobile telecommunications systems, to provide backup power to telecommunications systems and to provide remote residential power, among a myriad of other applications. Thus, DMFCs are capable of providing reliable and affordable power in remote locations. From an efficiency standpoint, current DMFC performance yields approximately 1 kilowatt average load for 3 months using about 500 gallons of fuel. Moreover, significant advances are expected in the near future increasing efficiency even further, bringing DMFCs ever closer to the forefront of power technology.

During operation of a fuel circulation loop for a DMFC, methanol and water are mixed in a fuel mixer, and it is important to the process that the concentration of methanol aqueous solution remains reasonably controlled throughout operation of the DMFC. In this regard, the rate by which methanol is added to the system is related to the rate of depletion of methanol in the system and thus, sensing the concentration of methanol so that an appropriate amount of methanol can be metered is desirable for such a process. Accordingly, there is a need for accurate measurement of fuel concentration in such a fuel cell system.

U.S. Pat. No. 6,306,285, to Narayanan et al., entitled "Techniques for Sensing Methanol Concentration in Aqueous Environments" (the '285 patent) discloses a technique for sensing methanol concentration, and provides a methanol concentration sensor device for coupling to a fuel metering control system for use in a liquid direct-feed fuel cell.

The method of the '285 patent teaches detecting a methanol compound concentration in an aqueous environment by using a sensor element to probe a liquid analyte solution including methanol to produce a sensor response. The sensor element includes an anode, a solid electrolyte membrane and a cathode. The sensor element also includes a catalyst, which is capable of chemically reacting with methanol. According to the method, the anode and cathode of the sensor element are immersed in the liquid analyte solution. An electrical power supply's positive terminal is connected to the anode and the electrical power supply's negative terminal is connected to the cathode. An analyte concentration sensing device is connected to the sensor element for detecting the response to the analyte, and is also connected electrically to the sensor element and the power supply in order to detect an amount of current consumed thereby. The method is alleged to be reliable in aqueous environments in the analyte concentration range 0.01 M to 5 M, and a temperature range of 0°–100° Celsius.

The sensors of the '285 patent, however, are relatively slow due to the time for the reactions to take place in the analyte solution. The need for a fast view of macroscopic change in concentration of methanol solution is thus undermined by the method taught by the '285 patent. Additionally, the sensor of the '285 is sensitive to both metallic and biological contaminants, skewing results undesirably. Since these contaminants further affect the operation of the DMFC itself due to a similar anode/cathode mechanism, over time, the use of the sensor of the '285 fails to serve as an impartial diagnostic tool. Moreover, additional plumbing and components are required that make such an implementation complex. For example, separate plumbing must be provided to the fuel samples and separate oxygen feed.

There are also other exhaustive techniques that are capable of measuring the concentration of methanol at a very high resolution. Since these techniques reproduce one or another principle of measurement of absolute physical value connected to absolute value of concentration, they are expensive and cumbersome, and thus not affordable and simple.

Thus, there is currently a strong need in the art for an improved system and methods for measuring the methanol-water mixture concentration accurately for a stand-alone DMFC. In this regard, there is a need in the art for simple, affordable and reliable methods for measuring methanol's concentration in aqueous solution in a DMFC fuel circulation loop.

SUMMARY OF THE INVENTION

In view of the foregoing, the present invention provides systems and methods for ultrasound sensing a compound's concentration in aqueous solution. As a result of the ultrasound sensing, an accurate real-time measurement of the concentration of the compound of interest in aqueous solution is obtained. In various non-limiting embodiments, the invention provides ultrasound sensing of methanol's concentration in aqueous solution in connection with a fuel circulation process for a direct methanol fuel cell. Since the speed of sound in a water-methanol system increases significantly with methanol content, techniques for measuring characteristic sound velocities are used to give sufficient resolution for a fuel circulation process.

Other aspects of the present invention are described below.

BRIEF DESCRIPTION OF THE DRAWINGS

The methods for sensing the concentration of methanol's aqueous solution with ultrasound are further described with reference to the accompanying drawings in which.

DETAILED DESCRIPTION OF THE INVENTION

Overview

As indicated above, there is currently a strong need in the art for a simple, reliable and affordable system and method that provides for accurate control of methanol-water mixture concentration for a stand-alone DMFC. No present system exists for measuring the concentration of methanol's aqueous solution by utilizing ultrasound, in an affordable and reliable manner. The advantages of ultrasound include relatively low cost, wide availability, safety, ease of use and real-time data processing.

In view of the various advantages associated with ultrasound techniques, the present invention provides methods of ultrasound sensing the concentration of methanol's aqueous solution in connection with the fuel circulation loop of a DMFC. Since the speed of sound in a water-methanol system increases significantly with methanol content in the concentration range 0% to 10% by weight, techniques are applied in accordance with the present invention to measure characteristic sound velocities of a fuel sample, giving sufficient resolution of the concentration measurements to control the fuel circulation loop of a DMFC process. It is understood that the techniques described herein may be applied to any application relating to the monitoring of small changes in concentration of a component of a liquid system that leads to an observable change of the speed of sound in the liquid.

Ultrasound Sensing of Methanol's Concentration

Concentration of methanol-water fuel solution circulating through the DMFC changes during the work process at a rate dependent on several factors, such as electrical load and temperature, resulting in a non-uniform consumption of methanol from the fuel solution. Thus, monitoring and control of fuel concentration are continuously performed during operation of a DMFC. Due to relatively slow changes in concentration, such monitoring and control may be performed within a sampling cycle in a range of one change per minute. This frequency is enough for full cycle measurement and control of the methanol concentration although it is understood that achieving a better, faster rate provides optimization benefits in terms of a simpler physical construction of the DMFC assembly as well as in terms of streamlining the operation of the DMFC. In order to provide effective control of the fuel circulation loop for a DMFC, the resolution of a sensor must be in the neighborhood of 0.1% by weight or better, since that is the level of control that is required to maintain a proper fuel mixture for the operation of a DMFC. The sensor device that achieves this resolution in accordance with the techniques of the present invention may be provided as part of DMFC assembly.

Figure 1A:
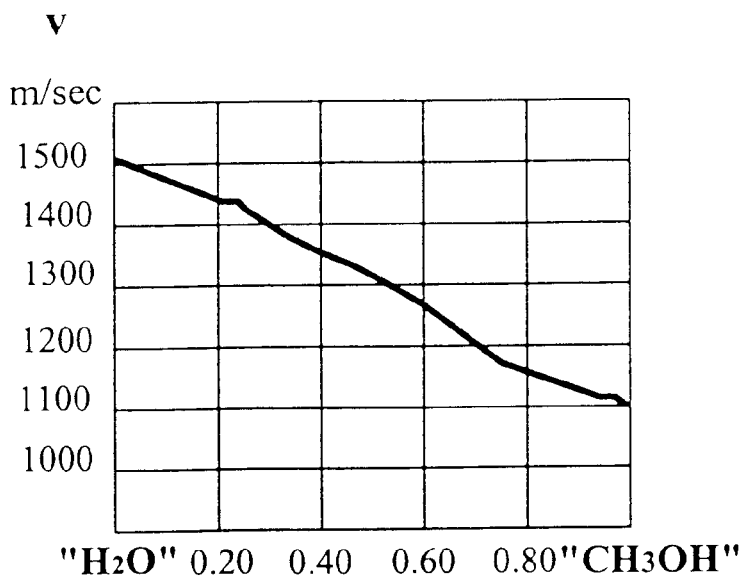
FIGS. 1A and 1B illustrate ideal and actual sound velocity curves for varying concentrations of methyl alcohol dissolved in water, respectively.
Figure 1B:
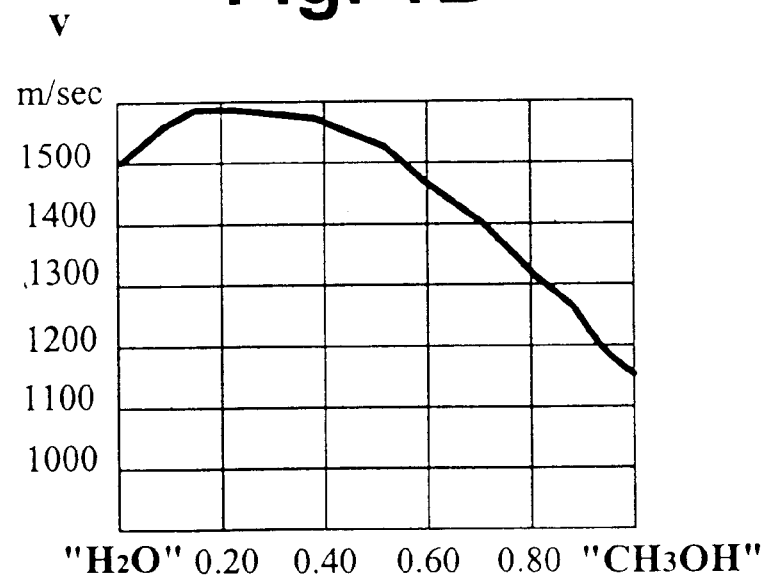

The methods of the present invention are based upon observed sound velocity vectors. This is achieved on the basis of existing dependencies between characteristic velocities (V) of longitudinal sound propagation and concentration in the water/methanol system. FIG. 1A illustrates the dependency of velocity on concentration for an 'ideal' unassociated liquid. FIG. 1B illustrates the dependency of velocity on concentration for methanol in aqueous solution. As one can see, due to strong hydrogen bonding of solute (methyl alcohol) and solvent (water) in this binary system, dependence of velocity on concentration is dramatically different from what is expected for unassociated liquids.

Based upon the ultrasound characteristics of FIG. 1B, the present invention provides methods for using an ultrasound sensor device to measure methanol's content in aqueous solution in the fuel circulation loop of a DMFC. The ultrasound sensor is designed based on observed sound velocity as the concentration of methanol changes in the range of 0.1% to 5% by weight, and is capable of achieving resolution to 0.1%.

The ultrasound devices and methods for using the same described herein provide low power consumption, compact instrumentation for determining the percentage concentration with a simple electrical analog output and can be used as a methanol concentration sensor in fuel cell systems. The analog output of the sensors can be analyzed directly or digitized and analyzed by a computing device, such as a microprocessor designed for the task An output of the processor based on the analog output may then be utilized as an input to the fuel circulation loop for controlling the amount of methanol being mixed in real-time. It is understood that a variety of devices, ranging from hardware to software, and from analog to digital, can perform the function of signal processing in accordance with the invention.

Figure 2A:
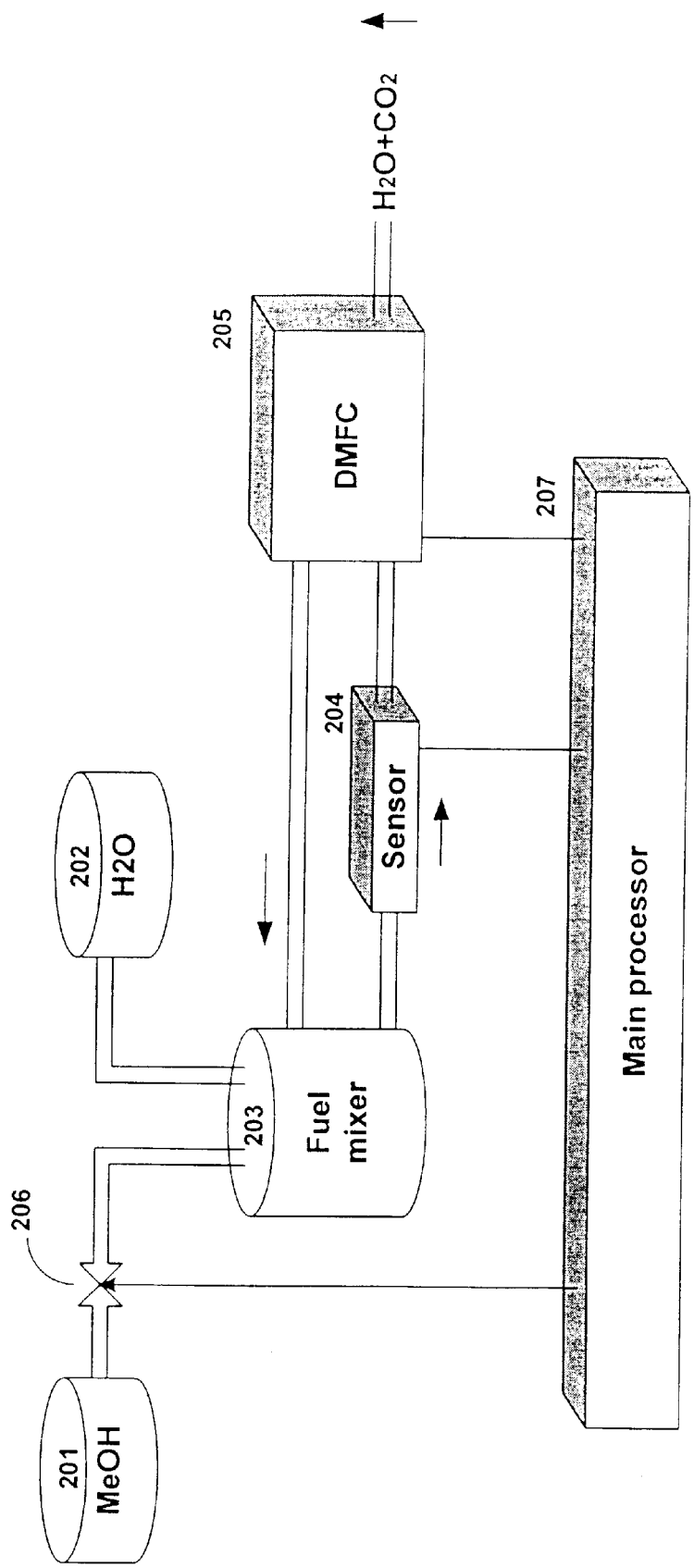
FIGS. 2A and 2B are diagrams of a fuel circulation process having ultrasound sensing of the concentration of methanol in aqueous solution in accordance with the present invention.

As mentioned above, ultrasound techniques are used to measure the concentration of methanol in aqueous solution in accordance with the present invention based upon observable differences in sound velocity in response to concentration changes. The 'in-line' location of this sensor in the DMFC layout may be understood from general diagram of FIG. 2A. In FIG. 2A, methanol, or MeOH, stock 201 and $H_2O$ stock 202 are mixed together in fuel mixer 203, whereby the flow controller 206 regulates the amount of methanol injected to the mix based on an input from the control processor 207. DMFC 205 partially consumes the fuel from fuel mixer 203, producing byproducts $H_2O$ and $CO_2$ and returning a fuel solution of unknown methanol concentration to fuel mixer 203. En route to DMFC 205, sample fuel from fuel mixer 203 is input to sensor 204, and output from sensor 204 to DMFC 205. The sensor may thus be provided as an in-line part of the DMFC system. Sensor 204 then utilizes ultrasound sensing techniques to compare an ultrasound measurement of the sample fuel to an ultrasound measurement of a reference liquid, such as pure water, and outputs a signal representative of the difference in sound velocity between the sample and reference liquid. This signal is an input to the main processor 207, which interprets the signal in terms of the methanol concentration of the fuel sample, and thus the fuel mix in the fuel mixer 203. Main processor 207 then outputs a corresponding control signal to the flow controller 206 based on the current consumption needs of DMFC 205.

Although fuel continuously circulates through the DMFC 205, the concentration of methanol-water fuel changes during the work due to several factors, such as electrical load, temperature changes, non-uniform consumption of fuel, etc. Therefore, monitoring and control of the fuel concentration are required while the DMFC 205 is operating. Due to relatively slow changes of concentration, measurements and controlling may be done within a sampling cycle in a range of one sample per minute. This frequency is enough for a full cycle of measurements and control.

Figure 2B:
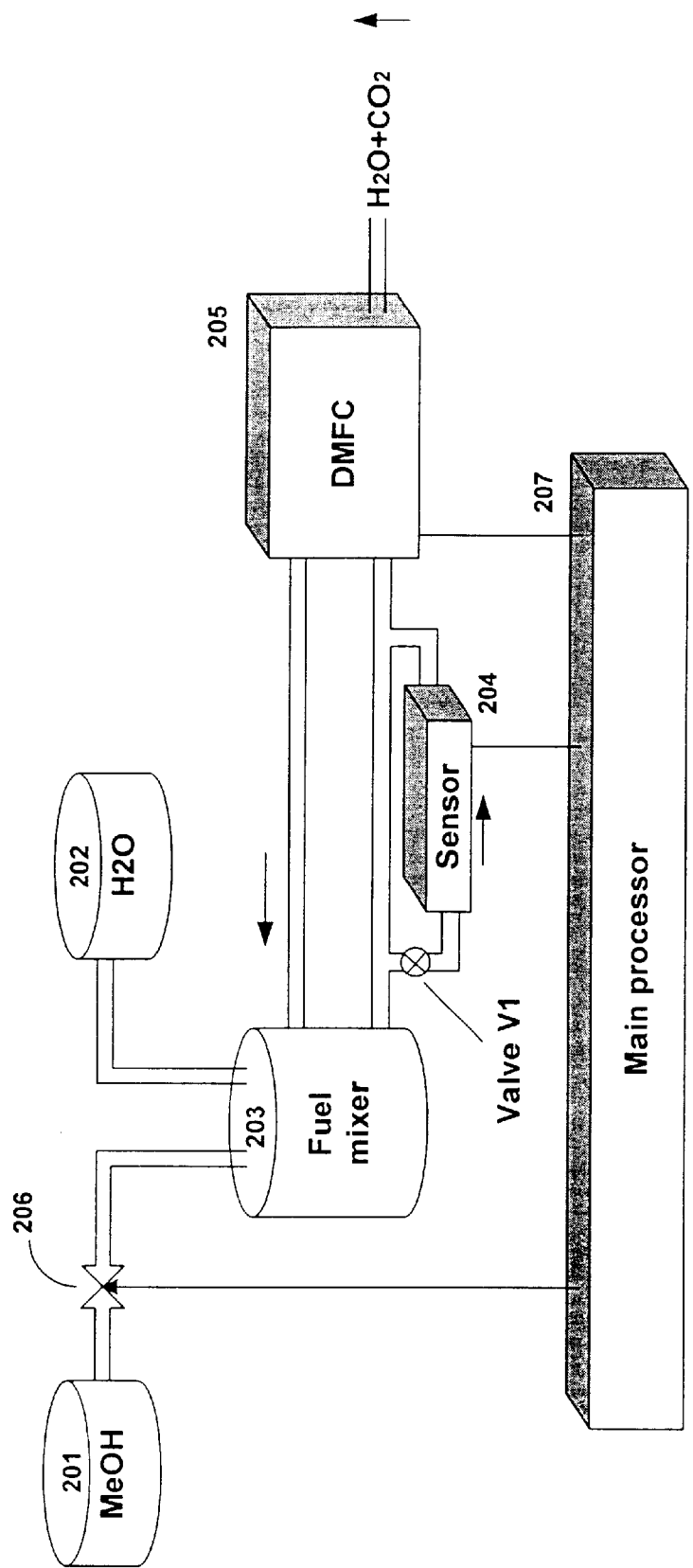

FIG. 2B illustrates another exemplary embodiment of the invention wherein the sensor 204 is piped parallel to the flow line from fuel mixer 203 to DMFC 205. In this case, a valve V1 is positioned at the fuel inlet, which may be invariably opened and closed to control the flow of fuel to sensor 204.

The method of concentration monitoring in the present invention assumes the ability to convert discrete sound velocity measurement data into numerical concentration data. The actual technique for sound velocity measurement is not critical to the invention as long as the technique is chosen to resolve the concentration differences sufficiently for the task. One satisfactory method for making the sound velocity measurement is based on the timing of sound pulse propagation along a known length.

Figure 3A:
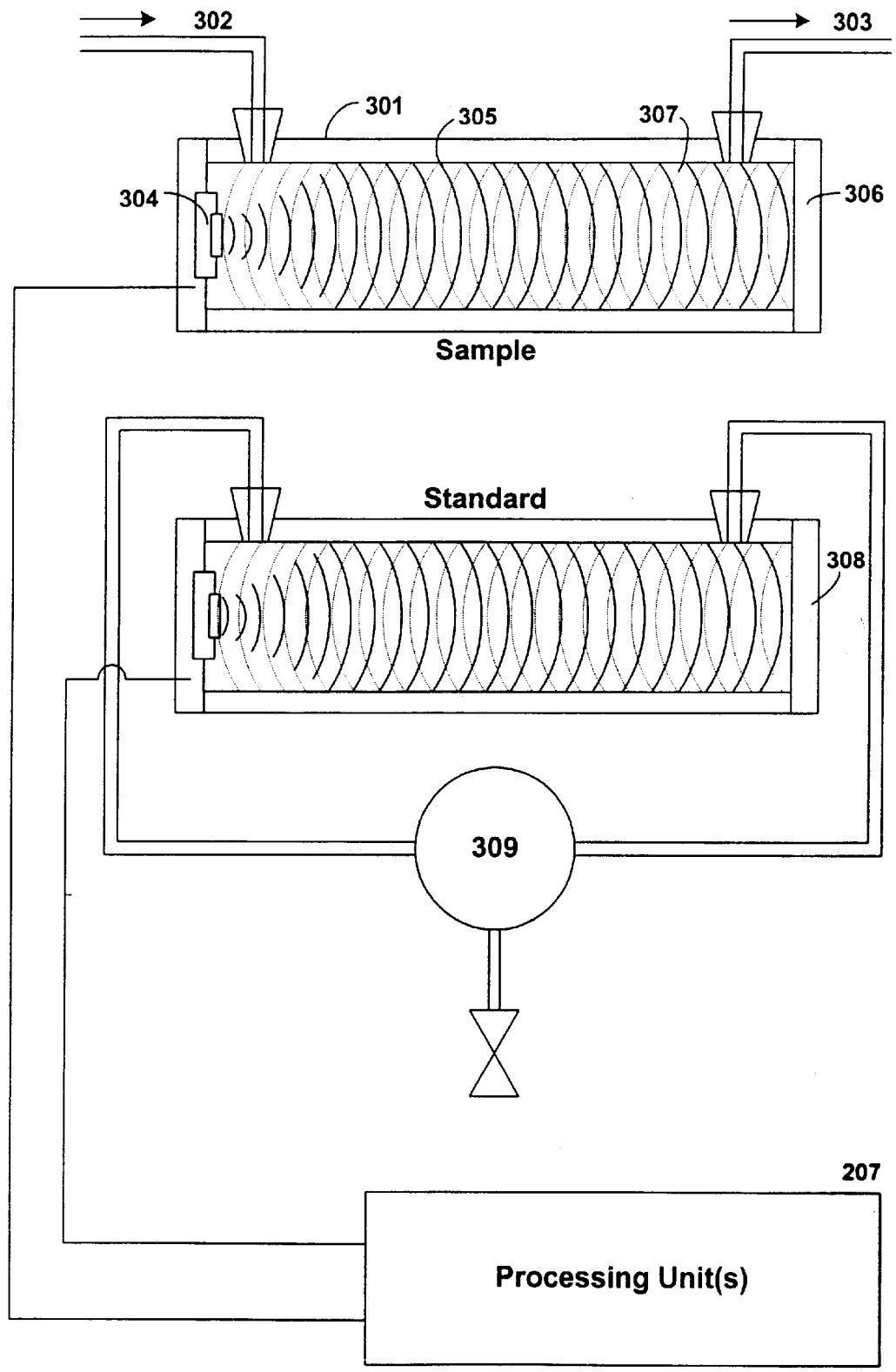
FIGS. 3A and 3B are diagrams of ultrasound sensing in accordance with the present invention in exemplary detail.

A more detailed view of the exemplary operation of ultrasound sensor 204 of FIG. 2A is depicted in FIG. 3A. FIG. 3A includes a fuel sample chamber 301 and a standard chamber 308, forming the differential assembly of the invention that reduces variation due to factors other than concentration changes. Inlet and outlet tubes 302 and 303, respectively, allow the fuel sample to enter and exit the sample chamber 301. For example, inlet tube 302 may transport fuel from fuel mixer 203 to the sample chamber 301 and outlet tube 303 may transport fuel from the sample chamber 301 to DMFC 205. In this embodiment, piezo-transducers 304, transmit ultrasound waves 305 which reflect off opposite sides 306 of the chambers 301 and 308 and propagate back 307 arriving at receiving parts of transducers 304. In this regard, standard chamber 308 is made identically to sample chamber 301, except that standard chamber 308 is connected in a closed loop manner with reservoir 309 having a standard liquid. As described above, processor 207 processes the information received from the receiving portions of transducers 304 and sends a control input signal to flow controller 206.

Figure 3B:
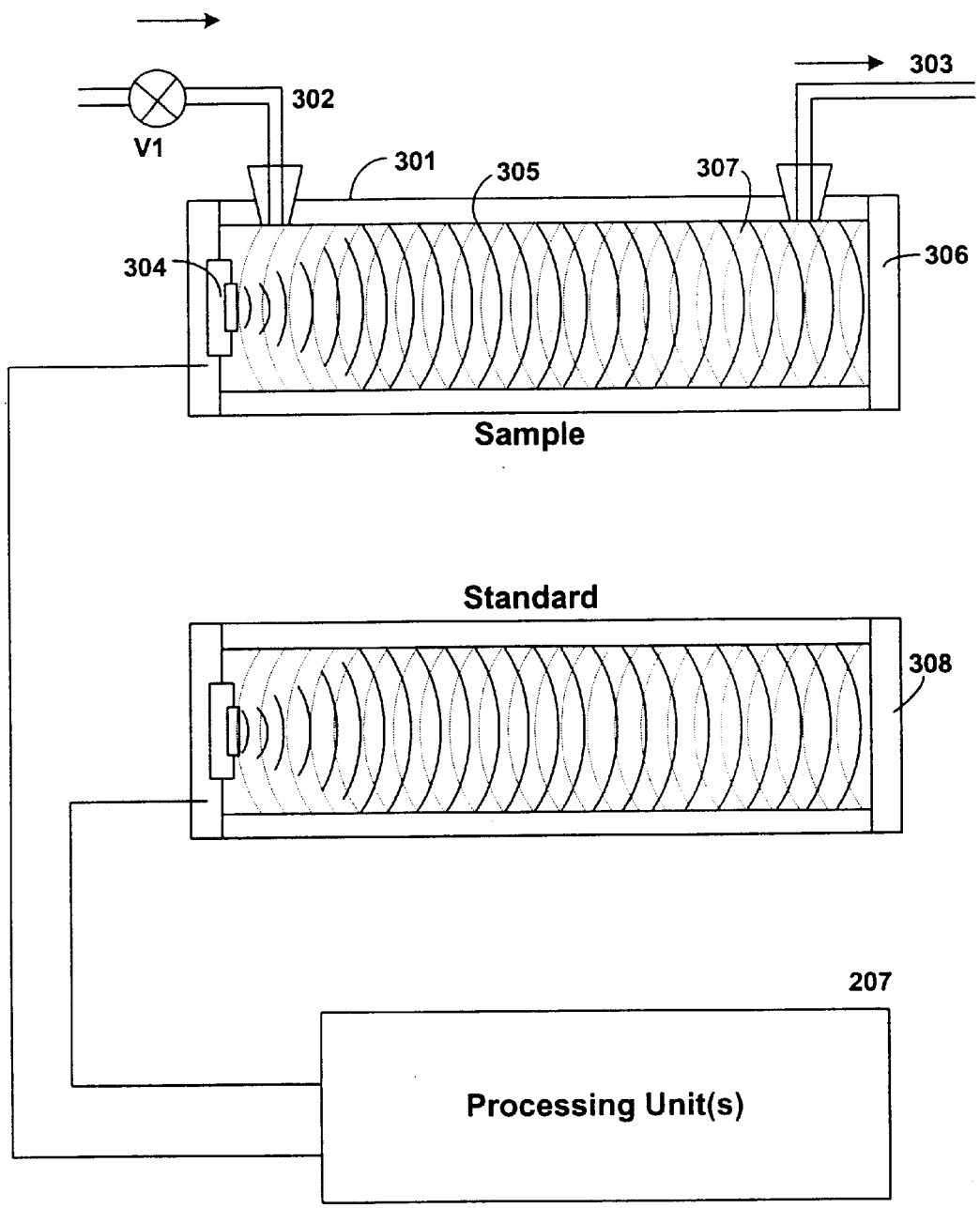

A more detailed view of the exemplary operation of ultrasound sensor 204 in the configuration of FIG. 2B is illustrated in FIG. 3B. In this parallel configuration, the reference chamber is a closed chamber of non-flowing reference fluid, such as water or a methanol solution having a fixed concentration. Valve V1 is positioned at the inlet of the sample chamber 301, and can periodically close, thereby stopping the flow of fuel solution in the sample chamber 301. While, or once, the fuel solution in the sample chamber 301 is filled, a comparative measurement is made in both the sample chamber 301 and standard chamber 308. The parallel configuration is desirable because it avoids the necessity of even monitoring, and/or even matching, flow rates in chambers 301 and 308.

The resolution of such a device in terms of a time-difference value, which also satisfies the resolution in the range 0.1% of concentration, may be estimated as follows. The slope of the velocity versus concentration curve $\Delta V/\Delta c$ is approximately 5 m/sec·%. If the length of propagation path L is equal to 0.5 m, then the difference between two periods of time corresponding to two methanol concentrations with difference $\Delta c=0.1\%$ is:

$$\Delta t=(L/V)-[L/V+\Delta V)]=(0.5 \text{ m}/1500 \text{ m/s})-[0.5 \text{ m/s}/(1500 \text{ m/s}+0.1\%*5 \text{ m/s·\%}]$$

This calculation yields a $\Delta t$ value of approximately $0.111*10^{-6}$ s.

Although a 100 ns range of time measurements is achievable with relative ease using conventional technology, special care should be taken with respect to temperature changes of the values contributing to the measurements. The temperature deviation of propagation path length for a material of a container may be as much as $10^{-4}$ deg$^{-1}$*100 deg * 0.5 m=0.005 m. Such a deviation corresponds to $\Delta t=0.333 \; 10^{-6}$ s and represents an obstacle. The remedy for temperature, or other nonstandard, deviations used by the present invention is a differential calculation using standard and sample chambers.

The differential calculation assumes two similar lines for sound pulse propagation, one of which is filled with the standard liquid, for example, pure water, and the other of which is filled with a sample liquid. The output signal in this arrangement is equal to the difference between $\Delta t_m$ for the sample liquid and $\Delta t_s$ for the standard one. Such an arrangement significantly decreases the influence of temperature changes, and other nonstandard variations in measurements, on final readings.

As far as the temperature dependence of the difference of the velocity for the standard and sample liquids is concerned, the processor 207 performs algorithmic compensation in accordance with known temperature dependence characteristics. Preliminary calibration for such temperature dependence can be obtained from averaging several simultaneous measurements of $\Delta t_m$ for sample liquid in chamber 301 and $\Delta t_s$ for the standard in chamber 308. Further conversion of numerical data for $(\Delta t_m - \Delta t_s)$ to the output of the sensor 204 may be accomplished with known techniques, and are not discussed herein.

In this regard, the rate of flow of the fuel sample through the sample chamber 301 and the rate of flow of the reference liquid through the reference chamber 308 are sufficient for full exchange of liquids within the time domain typical for the possible change of MeOH/$H_2O$ concentration in the fuel feed loop. The differential design enhances immunity to noise, changes in temperature, changes in pressure, etc. that may affect sound travel and operation of the sensor, and simplifies signal processing in terms of error correction.

Conclusion

While the present invention has been described in the context of measuring methanol's concentration in aqueous solution in connection with a DMFC fuel circulation process, the methods of the present invention can be used for any application related to monitoring small changes of concentration of a component of a liquid system, wherein the small changes lead to a corresponding change in sound velocity in the liquid.

It is understood that the methods and apparatus of the present invention may be implemented in many different forms. Thus, the present invention is by no means limited to any particular form of stock container 201 or 202, fuel mixer 203, DMFC 205, processor 207, flow controller 206, transducers 304, and so on. Moreover, it is apparent that the present invention may be practiced without necessarily using all of these components, or by replacing some or all of these with functional equivalents. Accordingly, the scope of protection of the following claims is not intended to be limited to the presently preferred embodiments described herein.

What is claimed is:

1. A method for ultrasound sensing the concentration of methanol in aqueous solution in connection with a fuel circulation loop of a direct methanol fuel cell, comprising:

transmitting by first and second transducers ultrasound waves through a fuel sample and a reference liquid in sample and reference chambers, respectively;

receiving by the first and second transducers the ultrasound waves reflected back through the fuel sample and reference liquid, respectively;

outputting first and second signals based upon the ultrasound waves reflected back and received by the first and second transducers, respectively;

processing the first and second signals with a processor to determine the concentration of methanol in the fuel sample; and inputting sample fuel to the sample chamber from a fuel mixer component of the fuel circulation loop.

2. A method according to claim 1, further including controlling the flow rate of methanol into a fuel mixer based upon the determined concentration.

3. A method according to claim 1, wherein the reference liquid is water.

4. A method according to claim 1, wherein the reference liquid is a fixed known concentration of methanol in water.

5. A method according to claim 1, wherein said transmitting includes transmitting said ultrasound waves by first and second piezo-transducers.

6. A method according to claim 1, further including outputting the sample fuel from the sample chamber to the direct methanol fuel cell for consumption.

7. An ultrasound sensing system for sensing the concentration of methanol in aqueous solution in connection with a fuel circulation loop of a direct methanol fuel cell, comprising:

a first ultrasound transducer for transmitting ultrasound waves through a fuel sample in a sample chamber, receiving the ultrasound waves that reflect back to the first ultrasound transducer and outputting a first signal based upon the ultrasound waves that reflect back;

a second ultrasound transducer for transmitting ultrasound waves through a reference liquid in a reference chamber and receiving the ultrasound waves that reflect back to the second ultrasound transducer and outputting a second signal based upon the ultrasound waves that reflect back; and a processor for processing the first and second signals to determine the concentration of methanol in the fuel sample, wherein said sample chamber includes an inlet tube for receiving the fuel sample and wherein the inlet tube receives the fuel sample from a fuel mixer component of the system.

8. A system according to claim 7, further including a flow rate controller that controls the flow rate of methanol into a fuel mixer based upon a control signal output by the processor after the processor determines the concentration of methanol in the fuel sample.

9. A system according to claim 7, wherein the reference liquid is water.

10. A system according to claim 7, wherein the reference liquid is a fixed known concentration of methanol in water.

11. A system according to claim 7, wherein said first and second transducers are first and second piezo-transducers.

12. A system according to claim 7, wherein the inlet tube to the sample chamber includes a valve.

13. A system according to claim 7, wherein said reference chamber includes an outlet tube for expelling fuel sample from the sample chamber.

14. A system according to claim 13, wherein the outlet tube expels fuel sample to the direct methanol fuel cell for consumption.

15. A method for ultrasound sensing the concentration of methanol in aqueous solution in connection with a fuel circulation loop of a direct methanol fuel cell, comprising:

transmitting by first and second transducers ultrasound waves through a fuel sample and a reference liquid in sample and reference chambers, respectively;

receiving by the first and second transducers the ultrasound waves reflected back through the fuel sample and reference liquid, respectively;

outputting first and second signals based upon the ultrasound waves reflected back and received by the first and second transducers, respectively;

processing the first and second signals with a processor to determine the concentration of methanol in the fuel sample; and outputting the sample fuel from the sample chamber to the direct methanol fuel cell for consumption.

16. A method according to claim 15, further including controlling the flow rate of methanol into a fuel mixer based upon the determined concentration.

17. A method according to claim 15, wherein the reference liquid is water.

18. A method according to claim 15, wherein the reference liquid is a fixed known concentration of methanol in water.

19. A method according to claim 15, wherein said transmitting includes transmitting said ultrasound waves by first and second piezo-transducers.

20. An ultrasound sensing system for sensing the concentration of methanol in aqueous solution in connection with a fuel circulation loop of a direct methanol fuel cell, comprising:

a first ultrasound transducer for transmitting ultrasound waves through a fuel sample in a sample chamber, receiving the ultrasound waves that reflect back to the first ultrasound transducer and outputting a first signal based upon the ultrasound waves that reflect back;

a second ultrasound transducer for transmitting ultrasound waves through a reference liquid in a reference chamber and receiving the ultrasound waves that reflect back to the second ultrasound transducer and outputting a second signal based upon the ultrasound waves that reflect back; and a processor for processing the first and second signals to determine the concentration of methanol in the fuel sample, wherein said reference chamber includes an outlet tube for expelling fuel sample from the sample chamber and wherein the outlet tube expels fuel sample to the direct methanol fuel cell for consumption.

21. A system according to claim 20, further including a flow rate controller that controls the flow rate of methanol into a fuel mixer based upon a control signal output by the processor after the processor determines the concentration of methanol in the fuel sample.

22. A system according to claim 20, wherein the reference liquid is water.

23. A system according to claim 20, wherein the reference liquid is a fixed known concentration of methanol in water.

24. A system according to claim 20, wherein said first and second transducers are first and second piezo-transducers.

25. A system according to claim 20, wherein said sample chamber includes an inlet tube for receiving the fuel sample.

26. A system according to claim 25, wherein the inlet tube to the sample chamber includes a valve.

* * * * *